US008614166B2

(12) United States Patent
Hacker et al.

(10) Patent No.: US 8,614,166 B2
(45) Date of Patent: *Dec. 24, 2013

(54) HERBICIDAL COMPOSITION FOR TOLERANT OR RESISTANT COTTON CROPS

(71) Applicant: Bayer Intellectual Property GmbH, Monheim (DE)

(72) Inventors: Erwin Hacker, Hochheim (DE); Hermann Bieringer, Eppstein (DE); Lothar Willms, Hofheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/680,617

(22) Filed: Nov. 19, 2012

(65) Prior Publication Data

US 2013/0079226 A1   Mar. 28, 2013

Related U.S. Application Data

(63) Continuation of application No. 09/371,769, filed on Aug. 10, 1999, now Pat. No. 8,338,332.

(30) Foreign Application Priority Data

Aug. 13, 1998  (DE) .................................. 19836659

(51) Int. Cl.
*A01N 57/00* (2006.01)
(52) U.S. Cl.
USPC .......................................... 504/127; 504/128
(58) Field of Classification Search
None
See application file for complete search history.

(56) References Cited

U.S. PATENT DOCUMENTS

| | | | |
|---|---|---|---|
| 4,265,654 A | 5/1981 | Takematsu et al. | |
| 4,822,401 A | 4/1989 | Tymonko et al. | |
| 5,198,599 A | 3/1993 | Thill et al. | |
| 5,273,894 A | 12/1993 | Strauch et al. | |
| 5,276,268 A | 1/1994 | Strauch et al. | |
| 5,599,769 A | 2/1997 | Hacker et al. | |
| 5,633,434 A | 5/1997 | Schneider et al. | |
| 5,885,936 A | 3/1999 | Zhang et al. | |
| 5,965,486 A | 10/1999 | Ruegg et al. | |
| 5,981,432 A | 11/1999 | Hudetz et al. | |
| 6,180,563 B1 | 1/2001 | Ruegg et al. | |
| 6,677,276 B1* | 1/2004 | Hacker et al. | 504/127 |
| 6,774,085 B1* | 8/2004 | Hacker et al. | 504/127 |
| 7,105,470 B1* | 9/2006 | Hacker et al. | 504/127 |
| 8,338,332 B1* | 12/2012 | Hacker et al. | 504/127 |
| 2001/0044382 A1 | 11/2001 | Ruegg et al. | |

FOREIGN PATENT DOCUMENTS

| | | |
|---|---|---|
| CA | 1291344 | 10/1991 |
| DE | 2856260 | 7/1979 |
| EP | 76470 | 4/1983 |
| EP | 0115673 | 8/1984 |
| EP | 0242236 | 10/1987 |
| EP | 0242246 | 10/1987 |
| EP | 0252237 | 1/1988 |
| EP | 0257542 | 3/1988 |
| EP | 0275957 | 7/1988 |
| EP | 0360750 | 3/1990 |
| EP | 0409815 | 1/1991 |
| WO | WO 91/11517 | 8/1991 |
| WO | WO 92/00377 | 1/1992 |
| WO | WO 92/08353 | 3/1992 |
| WO | WO 96/22692 | 8/1996 |
| WO | WO 96/32013 | 10/1996 |
| WO | WO 97/36488 | 10/1997 |
| WO | WO 98/09525 | 3/1998 |
| WO | WO 98/20144 | 5/1998 |

OTHER PUBLICATIONS

Katzek et al., Zuckerrübe, vol. 47, pp. 217-220, 1998.
The Pesticide Manual, 10$^{th}$ Edition, pp. 1335-1341.
English language abstract of WO 95/05082 published Feb. 23, 1995.
Database Accession No. 1998-72171.
Database Accession No. 1999-82695.
Database Accession No. 1994-81168.
Database Accession No. 1989-81729.
Database Accession No. 1989-81953.
Database Accession No. 1996-81471.

* cited by examiner

*Primary Examiner* — Alton Pryor
(74) *Attorney, Agent, or Firm* — Frommer Lawrence & Haug LLP

(57) ABSTRACT

Herbicide combinations (A)+(8), if appropriate in the presence of safeners, with an effective content of
(A) broad-spectrum herbicides from the group
  (A1) glufosinate (salts) and related compounds
  (A2) glyphosate (salts) and related compounds such as sulfosate,
  (A3) imidazolinones such as imazethapyr, imazapyr, imazaquin, imazamox or their salts and
  (A4) herbicidal azoles from the group of the protoporphyrinogen oxidase inhibitors (PPO inhibitors) and
  (A5) the hydroxybenzonitriles and
(B) herbicides from the group consisting of
  (B0) one or more structurally different herbicides from the abovementioned group (A),
  (B1) foliar- and soil-acting herbicides which are effective against monocotyledonous and dicotyledonous harmful plants,
  (B2) predominantly foliar-acting herbicides which are effective against dicotyledonous harmful plants,
  (B3) predominantly foliar-acting herbicides which are effective against monocotyledonous harmful plants, and
  (B4) foliar- and soil-acting herbicides which are effective against predominantly monocotyledonous harmful plants
for controlling harmful plants in tolerant or resistant mutants or transgenic cotton plants.

6 Claims, No Drawings

HERBICIDAL COMPOSITION FOR TOLERANT OR RESISTANT COTTON CROPS

The present application is a continuation of U.S. patent application Ser. No. 09/371,769 filed on Aug. 10, 1999, which claims priority from German Patent Application No. DE 198 36 659.0 filed on Aug. 13, 1998, the disclosures of which are incorporated herein by reference in their entirety.

The invention is in the field of the crop protection products which can be employed against harmful plants in tolerant or resistant crops of cotton and which comprise, as herbicidally active substances, a combination of two or more herbicides.

The introduction of tolerant or resistant cotton varieties and cotton lines, in particular transgenic cotton varieties and cotton lines, adds novel active substances which per se are not selective in conventional cotton varieties, to the conventional weed control system. The active substances are, for example, the known broad-spectrum herbicides such as glyphosate, sulfosate, glufosinate, bialaphos and imidazolinone herbicides [herbicides (A)], which can now be employed in the tolerant crops developed specifically for them. The efficacy of these herbicides against harmful plants in the tolerant crops is high, but depends—similarly to other herbicide treatments—on the nature of the herbicide employed, its application rate, the preparation in question, the harmful plants to be controlled, the climatic conditions, the soil conditions etc. Furthermore, the herbicides exhibit weak points (zero effect) against specific species of harmful plants. Another criterion is the duration of action, or the degradation rate of the herbicide. If appropriate, changes in the sensitivity of harmful plants, which may occur upon prolonged use of the herbicides or within a geographical limited area, must also be taken into consideration. The loss of action against individual plants can only be compensated for to some extent by higher application rates of the herbicides, if at all. Moreover, there is always a demand for methods to achieve the herbicidal effect with lower application rates of active substances. A lower application rate not only reduces the amount of an active substance required for application, but as a rule, also reduces the amount of formulation auxiliaries required. Both reduce the economic outlay and improve the eco-friendliness of the herbicide treatment.

Herbicide combinations (A)+(B), if appropriate in the presence of safeners, with an effective content of
(A) broad-spectrum herbicides from the group
  (A1) glufosinate (salts) and related compounds
  (A2) glyphosate (salts) and related compounds such as sulfosate,
  (A3) imidazolinones such as imazethapyr, imazapyr, imazaquin, imazamox or their salts and
  (A4) herbicidal azoles from the group of the protoporphyrinogen oxidase inhibitors (PPO inhibitors) and
  (A5) the hydroxybenzonitriles and
(B) herbicides from the group consisting of
  (B0) one or more structurally different herbicides from the above-mentioned group (A),
  (B1) foliar- and soil-acting herbicides which are effective against monocotyledonous and dicotyledonous harmful plants,
  (B2) predominantly foliar-acting herbicides which are effective against dicotyledonous harmful plants,
  (B3) predominantly foliar-acting herbicides which are effective against monocotyledonous harmful plants, and
  (B4) foliar- and soil-acting herbicides which are effective against predominantly monocotyledonous harmful plants are suitable for controlling harmful plants in cotton which consists of tolerant or resistant mutants or transgenic cotton plants.

One possibility for improving the use profile of a herbicide may consist in combining the active substance with one or more other active substances which contribute the desired additional properties. However, the combined use of a plurality of active substances does not infrequently lead to phenomena of a physical and biological incompatibility, for example lacking stability of a coformulation, decomposition of an active substance or antagonism of the active substances. In contrast, what is desired are combinations of active substances with a favorable profile of action, high stability and as synergistic an increased action as possible, which allows the application rate to be reduced in comparison with the individual application of the active substances to be combined.

Surprisingly, it has now been found that active substances from the group of the abovementioned broad-spectrum herbicides (A) in combination with other herbicides from group (A) and, if appropriate, specific herbicides (B) interact especially favorably when they are employed in the cotton crops which are suitable for the selective use of the first-mentioned herbicides.

The invention therefore relates to the use of herbicide combinations for controlling harmful plants in cotton crops, wherein the herbicide combination in question has a synergistically active content of (A) a broad-spectrum herbicide from the group of the compounds consisting of
  (A1) compounds of the formula (A1),

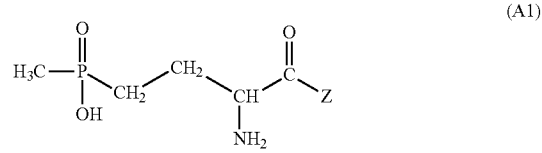

(A1)

in which Z is a radical of the formula —OH or a peptide radical of the formula —NHCH(CH$_3$)CONHCH(CH$_3$)COOH or —NHCH(CH$_3$)CONHCH[CH$_2$CH(CH$_3$)$_2$]COOH, and their esters and salts, preferably glufosinate and its salts with acids and bases, in particular glufosinate-ammonium, L-glufosinate or its salts, bialaphos and its salts with acids and bases, and other phosphinothricin derivatives, (A2) compounds of the formula (A2) and their esters and salts,

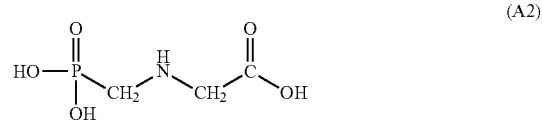

(A2)

preferably glyphosate and its alkali metal salts or salts with amines, in particular glyphosate-isopropylammonium, and sulfosates, (A3) imidazolinones, preferably imazethapyr, imazapyr, imazamethabenz, imazamethabenz-methyl, imazaquin, imazamox, imazapic (AC 263,222) and their salts and (A4) herbicidal azoles from the protoporphyrinogen-oxidase inhibitors (PPO inhibitors), such as WC9717 (=CGA276854), and (A5) hydroxybenzonitriles such as bromoxynil, and (B) one or more herbicides from the group of the compounds which consists of (B0) one or more structurally different herbicides from the above-mentioned group (A) and/or (B1) foliar- and soil-acting herbicides which are effective against monocotyledonous and dicotyledonous harmful plants, and/or (B2) predominantly foliar-acting herbicides which are effective against dicotyledonous harmful plants, and/or (B3) predominantly foliar-acting herbicides which are effective against monocotyledonous harmful plants, and/or (B4) foliar- and soil-acting herbicides which are effective against predominantly monocotyledonous harmful plants, and the cotton crops are tolerant to the herbicides (A) and (B) which form a constituent of the combination, if appropriate in the presence of safeners.

In addition to the herbicide combinations according to the invention, other crop protection active substances and adjuvants and formulation auxiliaries conventionally used in crop protection may be used.

The synergistic effects are observed when the active substances (A) and (B) are applied together, but can also be observed upon split application (splitting). Another possibility is to, apply the herbicides or herbicide combinations in several portions (sequential application), for example after pre-emergence applications, followed by post-emergence applications or after early post-emergence applications, followed by applications at medium or late post-emergence. Preferred is the simultaneous application of the active substances of the combination in question, if appropriate in several portions. However, a staggered application of the individual active substances of a combination is also possible and may be advantageous in individual cases. Other crop protection agents such as fungicides, insecticides, acaricides and the like, and/or different auxiliaries, adjuvants and/or fertilizer applications may also be integrated into this system application.

The synergistic effects allow the application rates of the individual active substances to be reduced, a more potent action against the same species of harmful plant combined with the same application rate, the control of species to which the action has hitherto not extended (zero effect), an extended application period and/or a reduced number of required individual applications and—as a result for the user—economical and ecologically more advantageous weed control systems.

For example, the combinations of (A)+(B) according to the invention allow synergistically increased effects which far and unexpectedly exceed the effects which can be achieved with the individual active substances (A) and (B).

WO-A-98/09525 has already described a method of controlling weeds in transgenic crops which are resistant to phosphorus-containing herbicides such as glufosinate or glyphosate, herbicide combinations being employed which comprise glufosinate or glyphosate and at least one herbicide from the group consisting of prosulfuron, primisulfuron, dicamba, pyridate, dimethenamid, metolachlor, flumeturon, propaquizafop, atrazine, clodinafop, norflurazone, ametryn, terbuthylazine, simazine, prometryn, NOA-402989 (3-phenyl-4-hydroxy-6-chloropyridazine), a compound of the formula

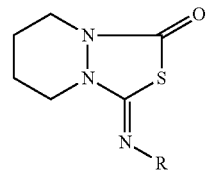

in which R=4-chloro-2-fluoro-5-(methoxycarbonylmethylthio)phenyl (disclosed in U.S. Pat. No. 4,671,819), CGA276854=1-allyloxycarbonyl-1-methylethyl 2-chloro-5-(3-methyl-2,6-dioxo-4-trifluoromethyl-3,6-dihydro-2H-pyrimidin-1-yl)-benzoate (=WC9717, disclosed in U.S. Pat. No. 5,183,492) and 4-oxetanyl 2-{N—[N-(4,6-dimethylpyrimidin-2-yl)aminocarbonyl]aminosulfonyl}benzoate (disclosed in EP-A-496701).

Details on the obtainable effects, or effects which have been obtained, cannot be found in the publication WO-A-98/09525. There are no examples on synergistic effects or on carrying out the method in specific crops, nor are there specific combinations of two, three or more herbicides.

DE-A-2856260 has already disclosed a few herbicide combinations with glufosinate or L-glufosinate and other herbicides such as alloxidim, linuron, MCPA, 2,4-D, dicamba, triclopyr, 2,4,5-T, MCPB and others.

Some herbicide combinations with glufosinate or glyphosate and other herbicides from the sulfonylurea series such as metsulfuron-methyl, nicosulfuron, primisulfuron, rimsulfuron and the like have already been disclosed in WO-A-92/08353 and EP-A 0 252 237.

However, the use of the combinations for controlling harmful plants has been shown in the publications only with reference to a few plants species or else with reference to no example.

In our experiments, it has been found, surprisingly, that there exist large differences between the usefulness of the herbicide combinations mentioned in WO-A-98/09525 and in the other publications and also of other novel herbicide combinations in crops of plants.

According to the invention, herbicide combinations which can be employed particularly advantageously in tolerant cotton crops are provided.

The compounds of the formulae (A1) to (A5) are known or can be prepared analogously to known processes.

Formula (A1) encompasses all stereoisomers and their mixtures, in particular the racemate and the particular enantiomer which has a biological action, for example L-glufosinate and its salts. Examples of active substances of the formula (A1) are the following:

(A1.1) glufosinate in the narrow sense, i.e. D,L-2-amino-4-[hydroxy(methyl)-phosphinyl]butanoic acid, (A1.2) glufosinate-monoammonium salt, (A1.3) L-glufosinate, L- or (2S)-2-amino-4-[hydroxy(methyl)phosphinyl]butanoic acid (phosphinothricin), (A1.4) L-glufosinate monoammonium salt, (A1.5) bialaphos (or bilanafos), i.e. L-2-amino-4-[hydroxy(methyl)phosphinyl]-butanoyl-L-alanyl-L-alanine, in particular its sodium salt.

The abovementioned herbicides (A1.1) to (A1.5) are absorbed via the green parts of the plants and are known as broad-range herbicides or total herbicides; they are inhibitors of the enzyme glutamine synthetase in plants; see "The Pesticide Manual" 11th Edition, British Crop Protection Council 1997, pp. 643-645 and 120-121. While they can be employed post-emergence for controlling broad-leaved weeds and grass weeds in plantation crops and on non-crop area and, using specific application techniques, also for the in-between-rows treatment of agricultural ground crops such as maize, cotton and the like, the importance of use as selective herbicides in resistant transgenic crops of plants is increasing.

Glufosinate is usually employed in the form of a salt, preferably of the ammonium salt. The racemate of glufosinate, or glufosinate-ammonium, alone is usually applied at rates between 50 and 2000 g of a.s./ha, usually 200 and 2000 g of a.s./ha (=g of a.s./ha=grams of active substance per hectare). At such rates, glufosinate is effective mainly when taken up via the green parts of the plants. However, since it is degraded microbially in the soil within a few days, it has no long-term action in the soil. The same also applies to the related active substance bialaphos sodium (also termed bilanafos-sodium); see "The Pesticide Manual" 11th Ed., British Crop Protection Council 1997 pp. 120-121.

As a rule, markedly less active substance (A1), for example an application rate in the range of 20 to 800, preferably 20 to 600, grams of active substance of glufosinate per hectare (g of a.s./ha or g of a.i./ha) is required in the combinations according to the invention. Similar amounts, preferably amounts which have been converted into moles per hectare, also apply to glufosinate-ammonium and bialafos, or bialafos-sodium.

The combinations with the foliar-acting herbicides (A1) are expediently employed in cotton crops which are resistant or tolerant to the compounds (A1). Some tolerant cotton crops which have been generated by genetic engineering, are already known and are employed in practice; cf. the article in the journal "Zuckerrübe" [Sugarbeet], year 47 (1998), p. 217 et seq.; for the generation of transgenic plants which are resistant to glufosinate, cf. EP-A-0242246, EP-A-242236, EP-A-257542, EP-A-275957, EP-A-0513054).

Examples of compounds (A2) are
(A2.1) glyphosate, i.e. N-(phosphonomethyl)glycine,
(A2.2) glyphosate-monoisopropylammonium salt,
(A2.3) glyphosate-sodium salt,
(A2.4) sulfosate, i.e. N-(phosphonomethyl)glycine-trimesium salt=N-(phosphonomethyl)glycine-trimethylsulfoxonium salt.

Glyphosate is usually employed in the form of a salt, preferably of the monoisopropylammonium salt or the trimethylsulfoxonium salt (=trimesium salt=sulfosate). Based on the free acid glyphosate, the single dose is in the range of 0.020-5 kg of a.s./ha, usually 0.5-5 kg of a.s./ha.

Glyphosate is similar to glufosinate with regard to certain applications, but, in contrast to the latter, it is an inhibitor of the enzyme 5-enolpyruvylshikimate-3-phosphate synthase in plants; see "The Pesticide Manual" 11th Ed., British Crop Protection Council 1997 pp. 646-649. In the combinations according to the invention, application rates in the range of 20 to 1000, preferably 20 to 800, g of a.s. glyphosate are, as a rule, required per ha.

Also, tolerant plants generated by genetic engineering are known for compounds (A2) and have been introduced into practice; cf. "Zuckerrübe" year 47 (1998), p. 217 et seq.; cf. also WO 92/00377, EP-A-115673, EP-A-409815.

Examples of imidazolinone herbicides (A3) are
(A3.1) imazapyr and its salts and esters,
(A3.2) imazethapyr and its salts and esters,
(A3.3) imazamethabenz and its salts and esters,
(A3.4) imazamethabenz-methyl,
(A3.5) imazamox and its salts and esters,
(A3.6) imazaquin and its salts and esters, for example the ammonium salt,
(A3.7) imazapic (AC 263,222) and its salts and esters, for example the ammonium salt.

The herbicides inhibit the enzyme acetolactate synthase (ALS) and thus the protein synthesis in plants; they are both soil-acting and foliar-acting and, in some cases, show selectivities in crops; cf. "The Pesticide Manual" 11th Ed., British Crop Protection Council 1997 pp. 697-699 for (A3.1), pp. 701-703 for (A3.2), pp. 694-696 for (A3.3) and (A3.4), pp. 696-697 for (A3.5), pp. 699-701 for (A3.6) and pp. 5 and 6, reviewed as AC 263,222 (for A3.7). The application rates of the herbicides are usually between 0.01 and 2 kg of a.s./ha, usually 0.1 and 2 kg of a.s./ha; especially (A3.1) from 20-400 g of a.s./ha, preferably 40-360 g of a.s./ha,
(A3.2) from 10-200 g of a.s./ha, preferably 20-180 g of a.s./ha,
(A3.3) from 100-2000 g of a.s./ha, preferably 150-1800 g of a.s./ha,
(A3.4) from 100-2000 g of a.s./ha, preferably 150-1800 g of a.s./ha,
(A3.5) from 1-150 g of a.s./ha, preferably 2-120 g of a.s./ha,
(A3.6) from 10-900 g of a.s./ha, preferably 20-800 g of a.s./ha,
(A3.7) from 5-2000 g of a.s./ha, preferably 10-1000 g of a.s./ha.

In the combinations according to the invention, they are in the range of 10 to 800 g of a.s./ha, preferably 10 to 200 g of a.s./ha.

The combinations with imidazolinones are expediently employed in cotton crops which are resistant to the imidazolinones. Such tolerant crops are already known. EP-A-0360750, for example, describes the generation of ALS-inhibitor-tolerant plants by selection methods or genetic engineering methods. The herbicide tolerance of the plants is generated by means of an elevated ALS content in the plants. U.S. Pat. No. 5,198,599 describes sulfonylurea- and imidazolinone-tolerant plants which have been obtained by selection methods.

Examples of PPO inhibitors (A4) are
(A4.1) pyraflufen and its esters, such as pyraflufen-ethyl,
(A4.2) carfentrazone and its esters, such as carfentrazone-ethyl,
(A4.3) oxadiargyl
(A4.4) sulfentrazone
(A4.5) WC9717 or CGA276854=1-allyloxycarbonyl-1-methylethyl 2-chloro-5-(3-methyl-2,6-dioxo-4-trifluoromethyl-3,6-dihydro-2H-pyrimidin-1-yl)-benzoate (disclosed in U.S. Pat. No. 5,183,492).

The abovementioned azoles are known as inhibitors of the enzyme protoporphyrinogen oxidase (PPO) in plants; see "The Pesticide Manual" 11th Ed., British Crop Protection Council 1997 pp. 1048-1049 for (A4.1), pp. 191-193 for (A4.2), pp. 904-905 for (A4.3) and pp. 1126-1127 for (A4.4). Tolerant crops of plants have already been described. As a rule, the application rates of the azoles are in the range of 1 to 1000 g of a.s./ha, preferably 2 to 800 g of a.s./ha, in particular the following application rates of the individual active substances:
(A4.1) 1 to 100, preferably 2 to 80 g of a.s./ha,
(A4.2) 1 to 500 g of a.s./ha, preferably 5-400 g of a.s./ha,
(A4.3) 10 to 1000 g of a.s./ha, preferably 20-800 g of a.s./ha,
(A4.4) 10 to 1000 g of a.s./ha, preferably 20-800 g of a.s./ha,
(A4.5) 10 to 1000 g of as/ha, preferably 20-800 g of a.s./ha.

Some plants which are tolerant to PPO inhibitors are already known.

An example of hydroxybenzonitriles (A5) is:
(A5.1) bromoxynil (see "The Pesticide Manual" 11th Ed., British Crop Protection Council 1997, pp. 149-151), i.e. 3,5-dibromo-4-hydroxybenzonitrile.

Hydroxybenzonitriles are photosynthesis inhibitors and are customarily employed at application rates of 50-3000 g of a.s./ha, preferably 50 to 2000 g of a.s./ha, in particular 100 to 2500 g of a.s./ha. Cotton plants which are tolerant to hydroxybenzonitriles such as bromoxynil are likewise known.

Examples of suitable components (B) are compounds of subgroups (B1) to (B4):

(B1) herbicides which are not only foliar-acting, but also soil-acting, and which can be employed against grasses and dicots, for example the following compounds (of which the common name and the reference in "The Pesticide Manual" 11th Ed., British Crop Protection Council 1997, abbreviated to "PM", is given; in the following, preferred application rates are also given in parentheses):

- (B1.1) norflurazon (PM, pp. 886-888), i.e. 4-chloro-5-(methylamino)-2-[3-(trifluoromethyl)phenyl]-3-(2H)-pyridazinone (from 500-6000, in particular 400-5000 g of a.s./ha)
- (B1.2) fluometuron (also "meturon", PM, pp. 578-579), i.e. N,N-dimethyl-N'-[3-(trifluoromethyl)phenyl]urea (from 100-3000, in particular 200-2500 g of a.s./ha);
- (B1.3) methylarsonic acid of the formula $CH_3As(=O)(OH)_2$ and its salts such as DSMA=disodium salt or MSMA=monosodium salt of methylarsonic acid (PM, pp. 821-823) (from 500-7000, in particular 600-6000 g of a.s./ha),
- (B1.4) diuron (PM, pp. 443-445), i.e. 3-(3,4-dichlorophenyl)-1,1-dimethylurea (from 100-5000, in particular 200-4000 g of a.s./ha),
- (B1.5) cyanazine (PM, pp. 280-283), i.e. 2-(4-chloro-6-ethylamino-1,3,5-triazin-2-ylamino)-2-methylpropionitrile (from 200-5000, in particular 300-4000 g of a.s./ha),
- (B1.6) prometryn (promethyrin) (PM, pp. 1011-1013), i.e. N,N'-bis(1-methylethyl)-6-methylthio)-2,4-diamino-1,3,5-triazine (from 50-5000, in particular 80-4000 g of a.s./ha),
- (B1.7) clomazone (PM, pp. 256-257), i.e. 2-(2-chlorobenzyl)-4,4-dimethyl-1,2-isoxazolidin-3-one (from 100-2000, in particular 150-1800 g of a.s./ha),
- (B1.8) trifluralin (PM, pp. 1248-1250), i.e. 2,6-dinitro-N,N-dipropyl-4-trifluoromethylaniline (from 200-4000, in particular 300-3000 g of a.s./ha),
- (B1.9) metolachlor (PM, pp. 833-834), i.e. 2-chloro-N-(2-ethyl-6-methyl phenyl)-N-(2-methoxy-1-methylethyl)acetamide (from 500-5000, in particular 800-4000 g of a.s./ha),
- (B1.10) linuron (PM, pp. 751-753), i.e. 3-(3,4-dichlorophenyl)-1-methoxy-1-methylurea (from 500-5000, in particular 800-4000 g of a.s./ha),
- (B1.11) paraquat (salts), e.g. the dichloride, (PM, pp. 923-925), i.e. 1,1'-(dimethyl)-4,4'-bipyridinium dichloride or other salts (from 50-2000, in particular 450-4000 g of a.s./ha) and/or
- (B1.12) pendimethalin (PM, pp. 937-939), i.e. N-(1-ethylpropyl)-2,6-dinitro-3,4-xylidine (from 100-5000, in particular 450-4000 g of a.s./ha), (B2) herbicides which can be employed against dicots, for example the compounds

- (B2.1) lactofen (PM, pp. 747-748), i.e. 2-ethoxy-1-ethyl-2-oxoethyl 5-[2-chloro-2-(trifluoromethyl)phenoxy]-2-nitrobenzoate (from 20-500, in particular 30-400 g of a.s./ha),
- (B2.2) oxyfluorfen (PM, pp. 919-921), i.e. 2-chloro-1-(3-ethoxy-4-nitrophenoxy)-4-(trifluoromethyl)benzene (from 50-1500, in particular 80-1200 g of a.s./ha) and/or
- (B2.3) bispyribac and its salts, e.g. the sodium salt, (PM, pp. 129-131), i.e. 2,6-bis(4,6-dimethoxypyrimidin-2-yloxy)-benzoic acid (from 5-300, in particular 10-200 g of a.s./ha) and/or, if appropriate,
- (B2.4) pyrithiobac and its salts, e.g. the sodium salt, (PM, pp. 1073-1075), i.e. sodium 2-chloro-6-(4,6-dimethoxypyrimidin-2-ylthio)benzoate (from 5-300, in particular 10-200 g of as/ha), (B3) herbicides which are predominantly foliar-acting and can be employed against monocotyledonous harmful plants, for example the compounds:

- (B3.1) quizalofop-P and its esters such as the ethyl or terfuryl ester (PM, pp. 1089-1092), i.e. (R)-2-[4-(6-chloroquinoxalin-2-yloxy)phenoxy]propionic acid or ethyl ester or tetrahydrofuryl ester (from 10-1500, in particular 20-1200 g of a.s./ha), also in the form of the mixtures with the S isomer, e.g. as racemic quizalofop and its esters,
- (B3.2) fenoxaprop-P and its esters such as the ethyl ester (PM, pp. 519-520), i.e. (R)-2-[4-(6-chlorobenzoxazol-2-yloxy)phenoxy]propionic acid or ethyl ester (from 10-300, in particular 20-250 g of a.s./ha), also in the form of the mixtures with the S isomer, e.g. as racemic fenoxaprop-ethyl,
- (B3.3) fluazifop-P and its esters such as the butyl ester (PM, pp. 556-557), i.e. (R)-2-[4-(5-trifluoromethyl-pyridyl-2-yloxy)phenoxy]propionic acid or butyl ester (from 20-1500, in particular 30-1200 g of a.s./ha); also in the form of the mixtures with the S isomer, e.g. as racemic fluazifop-butyl,
- (B3.4) haloxyfop and haloxyfop-P and their esters such as the methyl or the etotyl ester (PM, pp. 660-663), i.e. (R,S)- and (R)-2-[4-(3-chloro-5-trifluoromethyl-pyrid-2-yloxy)-phenoxy]propionic acid or methyl ester or etotyl ester (from 10-300, in particular 20-250 g of a.s./ha),
- (B3.5) propaquizafop (PM, pp. 1021-1022), i.e. isopropylideneaminooxyethyl (R)-2-[4-(6-chloroquinoxalin-2-yloxy)phenoxy]propionate (from 10-300, in particular 20-250 g of a.s./ha) and/or (B4) herbicides which are both foliar-acting and soil-acting and can be employed against monocotyledonous harmful plants, for example

- (B4.1) sethoxydim (PM, pp. 1101-1103), i.e. (E,Z)-2-(1-ethoxyiminobutyl)-5-[2-(ethylthio)-propyl]-3-hydroxy-cyclohex-2-enone (from 50-3000, in particular 100-2000 g of a.s./ha),
- (B4.2) cycloxydim (PM, pp. 290-291), i.e. 2-(1-ethoxyiminobutyl)-3-hydroxy-5-thian-3-ylcyclohex-2-enone (from 10-1000, in particular 30-800 g of a.s./ha),
- (B4.3) clethodim (PM, pp. 250-251), i.e. 2-{(E)1-[(E)-3-chloroallyloxyimino]propyl}-5-[-2(ethylthio)propyl]-3-hydroxycyclohex-2-enone (from 10-800, in particular 20-600 g of a.s./ha).

The application rates of the herbicides (B) may vary greatly from herbicide to herbicide. The following ranges are rules of thumb:

Compounds (B0): 5-2000 g of a.s./ha (cf. the information on the group of the compounds (A)

Compounds (B1): 50-7000 g of a.s./ha, preferably 20-5000 g of a.s./ha,

Compounds (B2): 5-5000 g of a.s./ha, preferably 20-5000 g of a.s./ha in particular 20-1200 g of a.s./ha, Compounds (B3): 10-1500 g of a.s./ha, preferably 5-500 g of a.s./ha Compounds (B4): 10-3000 g of a.s./ha, preferably 5-1000 g of a.s./ha.

The ratios of compounds (A) and (B) can be deduced from the above-mentioned application rates for the individual substances, for example the following ratios are of particular interest:

(A):(B) in the range of 400:1 to 1:1000, preferably of 200:1 to 1:100, (A):(B0) preferably of 400:1 to 1:400, in particular 200:1 to 1:200, (A1):(B1) of 300:1 to 1:400, preferably 200:1 to 1:300, in particular 100:1 to 1:50, very particularly of 50:1 to 1:20, (A1):(B2) of 500:1 to 1:100, preferably of 100:1 to 1:50, in particular of 50:1 to 1:20, (A1):(B3) of 400:1 to 1:400, preferably of 200:1 to 1:200, in particular of 200:1 to 1:100, (A1):(B4) of 200:1 to 1:200, preferably of 200:1 to 1:100, in particular of 100:1 to 1:50, (A2):(B1) of 200:1 to 1:50, preferably 100:1 to 1:50, in particular of 60:1 to 1:20, (A2):(B2) of 400:1 to 1:100, preferably of 200:1 to 1:50, in particular of 60:1 to 1:20, (A2):(B3) of 500:1 to 1:100, preferably of 200:1 to 1:100, in particular of 100:1 to 1:50, (A2):(B4) of 300:1 to 1:100, preferably of 200:1 to 1:70, in particular of 100:1 to 1:50, (A3):(B1) of 20:1 to 1:500, preferably 10:1 to 1:100, in particular 5:1 to 1:20, (A3):(B2) of 100:1 to 1:500, preferably 100:1 to 1:200, in particular of 10:1 to 1:100, (A3):(B3) of 50:1 to 1:200, preferably 50:1 to 1:50, in particular of 20:1 to 1:20, (A3):(B4) of 40:1 to 1:300, preferably of 20:1 to 1:100, in particular of 10:1 to 1:50, (A4):(B1) of 100:1 to 1:1000, preferably of 20:1 to 1:1000, in particular of 10:1 to 1:500, (A4):(B2) of 100:1 to 1:1000, preferably of 20:1 to 1:1000, in particular of 10:1 to 1:500, (A4):(B3) of 100:1 to 1:200, preferably of 50:1 to 1:100, in particular of 10:1 to 1:20, (A4):(B4) of 50:1 to 1:300, preferably of 20:1 to 1:200, in particular of 10:1 to 1:100, (A5):(B1) preferably of 100:1 to 1:100, in particular of 10:1 to 1:10, (A5):(B2) of 500:1 to 1:150, preferably of 100:1 to 1:100, in particular of 10:1 to 1:10, (A5):(B3) preferably of 400:1 to 1:10, in particular of 100:1 to 1:5, (A5):(B4) of 400:1 to 1:50, preferably of 200:1 to 1:20, in particular of 100:1 to 1:10.

The use of the following combinations is of particular interest:

(A1.1)+(B1.1), (A1.1)+(B1.2), (A1.1)+(B1.3), (A1.1)+(B1.4), (A1.1)+(B1.5),
(A1.1)+(B1.6), (A1.1)+(B1.7), (A1.1)+(B1.8), (A1.1)+(B1.9), (A1.1)+(B1.10),
(A1.1)+(B1.11), (A1.1)+(B1.12),
(A1.2)+(B1.1), (A1.2)+(B1.2), (A1.2)+(B1.3), (A1.2)+(B1.4), (A1.2)+(B1.5),
(A1.2)+(B1.6), (A1.2)+(B1.7), (A1.2)+(B1.8), (A1.2)+(B1.9), (A1.2)+(B1.7),
(A1.2)+(B1.7), (A1.2)+(B1.8), (A1.2)+(B1.9), (A1.2)+(B1.10), (A1.1)+(B1.11),
(A1.1)+(B1.12),
(A1.1)+(B2.1), (A1.1)+(B2.2), (A1.1)+(B2.3), (A1.1)+(B2.4),
(A1.2)+(B2.1), (A1.2)+(B2.2), (A1.2)+(B2.3), (A1.2)+(B2.4),
(A1.1)+(B3.1), (A1.1)+(B3.2), (A1.1)+(B3.3), (A1.1)+(B3.4), (A1.1)+(B3.5),
(A1.2)+(B3.1), (A1.2)+(B3.2), (A1.2)+(B3.3), (A1.2)+(B3.4), (A1.2)+(B3.5),
(A1.1)+(B4.1), (A1.1)+(B4.2), (A1.1)+(B4.3),
(A1.2)+(B4.1), (A1.2)+(B4.2), (A1.2)+(B4.3),
(A2.2)+(B1.1), (A2.2)+(B1.2), (A2.2)+(B1.3), (A2.2)+(B1.4), (A2.2)+(B1.5),
(A2.2)+(B1.6), (A2.2)+(B1.7), (A2.2)+(B1.8), (A2.2)+(B1.9), (A2.2)+(B1.10),
(A2.2)+(B1.11), (A1.1)+(B1.12),
(A2.2)+(B2.1), (A2.2)+(B2.2), (A2.2)+(B2.3), (A2.2)+(B2.4),
(A2.2)+(B3.1), (A2.2)+(B3.2), (A2.2)+(B3.3), (A2.2)+(B3.4), (A2.2)+(B3.5),
(A2.2)+(B4.1), (A2.2)+(B4.2), (A2.2)+(B4.3).

In the case of the combination of a compound (A) with one or more compounds (B0), this is, according to the definition, a combination of two or more compounds from group (A). Because of the broad-spectrum herbicides (A), the condition for such a combination is that the transgenic plants or mutants show cross-resistance to various herbicides (A). Such cross-resistances in transgenic plants have already been disclosed; cf. WO-A-98/20144.

In individual cases, it may be meaningful to combine one or more of the compounds (A) with more than one compound (B), preferably from amongst classes (B1), (B2), (B3) and (B4).

Moreover, the combinations according to the invention can be employed together with other active substances, for example from the group of the safeners, fungicides, insecticides and plant growth regulators, or from the group of the additives and formulation auxiliaries conventionally used in crop protection.

Additives are, for example, fertilizers and colors.

Preferred are herbicide combinations of one or more compounds (A) with one or more compounds from the group (B1) or (B2) or (B3) or (B4).

Also preferred are combinations of one or more compounds (A), for example (A1.2)+(A2.2), preferably of a compound (A), with one or more compounds (B) as shown in the scheme:

(A)+(B1)+(B2), (A)+(B1)+(B3), (A)+(B1)+(B4), (A)+(B2)+(B3),
(A)+(B2)+(B4), (A)+(B3)+(B4), (A)+(B1)+(B2)+(B3),
(A)+(B1)+(B2)+(B4), (A)+(B1)+(B3)+(B4), (A)+(B2)+(B3)+(B4).

Combinations to which one or more other active substances of a different structure [active substances (C)] are added are also according to the invention, for example (A)+(B1)+(C), (A)+(B2)+(C), (A)+(B3)+(C) or (A)+(B4)+(C),
(A)+(B1)+(B2)+(C), (A)+(B1)+(B3)+(C), (A)+(B1)+(B4)+(C),
(A)+(B2)+(B4)+(C) or (A)+(B3)+(B4)+(C).

The preferred conditions illustrated hereinbelow also apply to combinations of the last-mentioned type with three or more active substances, in particular to two-way-combinations according to the invention, mainly when they contain the two-way-combinations according to the invention and with respect to the relevant two-way-combinations.

The use according to the invention of the combinations with a herbicide from the group (A), preferably (A1.2) or (A2.2), in particular (A1.2), and with one or more herbicides, preferably one herbicide, from the group mentioned hereinbelow is also of particular interest:

(B0') one or more structurally different herbicides from the abovementioned group (A)

(B1') methylarsonic acid, diuron, cyanazine, clomazone, trifluralin, paraquat and/or pendimethalin and/or (B2') lactofen, oxyfluorfen and/or bispyribac and/or, if appropriate, pyrithiobac and/or (B3') quizalofop-P and its esters, quizalofop and its esters, fenoxaprop-P and its esters, fenoxaprop and its esters, fluazifop-P and its esters, fluazifop and its esters, haloxyfop and its esters and/or haloxyfop-P and its esters and/or (B4') sethoxydim, cycloxydim and/or clethodim.

Preferred are the combinations of the particular component (A) with one or more herbicides of group (B1'), (B2'), (B3') or (B4').

Also preferred are the combinations (A)+(B1')+(B2'), (A)+(B1')+(B3'), (A)+(B1')+(B4'), (A)+(B2')+(B3'), (A)+(B2')+(B4') or (A)+(B3')+(B4').

The combinations according to the invention (=herbicidal compositions) have an outstanding herbicidal activity against a broad spectrum of economically important monocotyledonous and dicotyledonous harmful plants. The active substances also act efficiently on perennial weeds which produce shoots from rhizomes, rootstocks or other perennial organs and which are difficult to control. In this context, it does not matter whether the substances are applied before sowing, pre-emergence or post-emergence. Post-emergence application, or early post-sowing pre-emergence application, is preferred.

Specifically, examples may be mentioned of some representatives of the monocotyledonous and dicotyledonous weed flora which can be controlled by the compounds according to the invention, without the enumeration being a restriction to certain species. Examples of weed species on which the herbicidal compositions act efficiently are, from amongst the monocots, *Echinochloa* spp., *Setaria* spp., *Digitaria* spp., *Brachilisia* spp., *Sorghum* spp. and *Cynodon* spp., but also *Agropyron* spp., wild cereal forms, *avena* spp., *Alopecurus* spp., *Lolium* spp., *Phalaris* spp., *Poa* spp., and *Cyperus* species and *Imperata*.

In the case of the dicotyledonous weed species, the spectrum of action extends to species such as, for example, *Chenopodium* spp., *Amaranthus* spp., *Solanum* spp., *Datura* spp., *Cupsella* spp. and *Cirsium* spp., But also *Abutilon* spp., *Chrysanthemum* spp., *Matricaria* spp., *Kochia* spp., *Veronica* spp., *Viola* spp., *Anthemis* spp., *Stellaria* spp., *Thlaspi* spp., *Galium* spp., *Ipomoea* spp., *Lamium* spp., *Pharbitis* spp., *Sida* spp., *Sinapis* spp., *Convolvulus, Rumex* and *Artemisia*.

If the compounds according to the invention are applied to the soil surface before germination, then the weed seedlings are either prevented completely from emerging, or the weeds grow until they have reached the cotyledon stage but then their growth stops, and eventually, after three to four weeks have elapsed, they die completely.

If the active substances are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

In comparison with the individual preparations, the herbicidal compositions according to the invention are distinguished by a more rapidly commencing and longer lasting herbicidal action. As a rule, the rainfastness of the active substances in the combinations according to the invention is advantageous. A particular advantage is that the dosages of the compounds (A) and (B), which are used in the combinations and are effective, can be adjusted to such a low quantity that their soil action is optimal. This does not only allow them to be employed in sensitive crops in the first place, but groundwater contaminations are virtually avoided. The active-substance-combination according to the invention allows the application rate of the active substances required to be reduced considerably.

When herbicides of the type (A)+(B) are used jointly, superadditive (=synergistic) effects are observed. This means that the effect in the combinations exceeds the expected total of the effects of the individual herbicides employed. The synergistic effects allow the application rate to be reduced, a broader spectrum of broad-leaved weeds and grass weeds to be controlled, the herbicidal effect to take place more rapidly, the duration of action to be longer, the harmful plants to be controlled better while using only one, or few, applications, and the application period which is possible to be extended. In some cases, uptake of the compositions also reduces the amount of harmful constituents in the crop plant, such as nitrogen or oleic acid. The abovementioned properties and advantages are necessary under practical weed control conditions to keep agricultural crops free from undesired competing plants and thus to guarantee and/or increase the yields from the qualitative and quantitative point of view. These novel combinations markedly exceed the technical state of the art with a view to the properties described.

While the compounds according to the invention have an outstanding herbicidal activity against monocotyledonous and dicotyledonous weeds, the tolerant, or cross-tolerant, cotton plants are damaged only to a minor extent, or not at all.

Moreover, some of the compositions according to the invention have outstanding growth-regulatory properties on the cotton plants. They engage in the plants' metabolism in a regulatory manner and can thus be employed for provoking directed effects on plant constituents. Moreover, they are also suitable for the general control and inhibition of undesired vegetative growth without simultaneously destroying the plants. An inhibition of vegetative growth is very important in a large number of monocotyledonous and dicotyledonous crops since lodging can thus be reduced, or prevented completely.

Owing to their herbicidal and plant-growth-regulatory properties, the compositions can be employed for controlling harmful plants in known tolerant or cross-tolerant cotton crops, or in tolerant or genetically engineered cotton crops still to be developed. As a rule, the transgenic plants are distinguished by particular, advantageous properties, in addition to resistances to the compositions according to the invention, for example, by resistances to plant diseases or pathogens of plant diseases such as particular insects or microorganisms such as fungi, bacteria or viruses. Other particular properties relate, for example, to the harvested material with regard to quantity, quality, storability, composition and specific constituents. Thus, transgenic plants are known whose oil content is increased or whose quality is altered, for example where the harvested material has a different fatty acid composition.

Conventional methods of generating novel plants which have modified properties in comparison to plants occurring to date consist, for example, in traditional breeding methods and the generation of mutants. Alternatively, novel plants with altered properties can be generated with the aid of genetic engineering methods (see, for example, EP-A-0221044, EP-A-0131624). For example, the following were described in several cases:

the modification, by genetic engineering, of crop plants with the aim of modifying the starch synthesized in the plant (for example WO 92/11376, WO 92/14827, WO 91/19806), transgenic crop plants which exhibit resistances to other herbicides, for example to sulfonylureas (EP-A-0257993, U.S. Pat. No. 5,013,659), transgenic crop plants with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972).

A large number of techniques in molecular biology with the aid of which novel transgenic plants with modified properties can be generated are known in principle; see, for example, Sambrook et al., 1989, Molecular Cloning, A Laboratory Manual, 2nd Edition, Cold Spring Harbor Laboratory Press, Cold Spring Harbor, N.Y.; or Winnacker "Gene und Klone" [Genes and Clones], VCH Weinheim 2nd Edition 1996 or Christou, "Trends in Plant Science" 1 (1996) 423-431.

To carry out such genetic engineering manipulations, nucleic acid molecules which allow mutagenesis or sequence changes by recombination of DNA sequences can be introduced in plasmids. For example, the abovementioned standard methods allow base changes to be carried out, subsequences to be removed, or natural or synthetic sequences to be added. To connect the DNA fragments to each other, adaptors or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the above-mentioned gene product.

To this end, it is possible to use, on the one hand, DNA molecules which encompass the entire encoding sequence of a gene product inclusive of any flanking sequences which may be present, as well as DNA molecules which only encompass portions of the encoding sequence, it being necessary for these portions to be long enough to have an antisense effect on the cells. The use of DNA sequences which have a high degree of homology to the encoding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the encoding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give rise to whole plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

The invention therefore also relates to a method of controlling undesired vegetation in tolerant cotton crops, which comprises applying one or more herbicides of the type (A) and one or more herbicides of the type (B) to the harmful plants, parts of these plants, or the area under cultivation.

The invention also relates to the novel combinations of compounds (A)+(B) and to herbicidal compositions comprising them.

The active substance combinations according to the invention can exist not only as formulation mixes of the two components, if appropriate together with other active substances, additives and/or conventional formulation auxiliaries, which are then applied in the customary manner after dilution with water, but also as so-called tank mixes by jointly diluting the separately formulated, or partially separately formulated, components with water.

Compounds (A) and (B) or their combinations can be formulated in different ways, depending on the biological and/or chemico-physical parameters which prevail. The following are examples of general possibilities for formulations: wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed-dressing materials, granules for soil application or for broadcasting, or water dispersible granules (WG), ULV formulations, microcapsules or waxes.

The individual formulation types are known in principle and are described, for example, in: Winnacker-Küchler "Chemische Technologie" [Chemical engineering], Volume 7, C. Hauser Verlag Munich, 4th Edition, 1986; van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y. Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976, Winnacker-Küchler, "Chemische Technologie", Volume 7, C. Hauser Verlag Munich, 4th Edition 1986.

Based on these formulations, combinations with other pesticidally active substances, such as other herbicides, fungicides or insecticides, and with safeners, fertilizers and/or growth regulators, may also be prepared, for example in the form of a readymix or a tank mix.

Wettable powders (sprayable powders) are products which are uniformly dispersible in water and which, besides the active substance, also comprise ionic or non-ionic surfactants (wetters, dispersants), for example polyoxethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltauride, in addition to a diluent or inert material.

Emulsifiable concentrates are prepared by dissolving the active substance in an organic solvent, for example butanol, cyclohexanone, dimethylformamide, xylene or else higher-boiling aromatic or hydrocarbons with addition of one or more ionic or non-ionic surfactants (emulsifiers). Examples of emulsifiers which may be used are: calcium salts of alkylarylsulfonic acids, such as calcium dodecylbenzene sulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxethylene sorbitol esters.

Dusts are obtained by grinding the active substance with finely divided solid materials, for example talc, natural clays such as kaolin, bentonite and pyrophyllite, or diatomateous earth.

Granules can be prepared either by spraying the active substance onto adsorptive, granulated inert material or by applying active substance concentrates to the surface of carriers such as sand, kaolites or granulated inert material with the aid of binders, for example polyvinyl alcohol, sodium polyacrylate or else mineral oils. Suitable active substances may also be granulated in the manner conventionally used for the production of fertilizer granules, if desired in a mixture with fertilizers. As a rule, water-dispersible granules are prepared by processes such as spray drying, fluidized-bed granulation, disk granulation, mixing with high-speed mixers and extrusion without solid inert material.

As a rule, the agrochemical preparations comprise 0.1 to 99 percent by weight, in particular 2 to 95% by weight, of active substances of the types A and/or B, the following concentrations being customary, depending on the type of formulation:

The active substance concentration in wettable powders, is, for example, approximately 10 to 95% by weight, the remainder to 100% by weight being composed of customary formulation constituents. In the case of emulsifiable concentrates, the active substance concentration may amount to, for example, 5 to 80% by weight.

Formulations in the form of dusts comprise, in most cases, 5 to 20% by weight of active substance, sprayable solutions approximately 0.2 to 25% by weight of active substance.

In the case of granules such as dispersible granules, the active substance content depends partly on whether the active compound is present in liquid or solid form and on which granulation auxiliaries and fillers are being used. As a rule, the content amounts to between 10 and 90% by weight in the case of the water-dispersible granules.

In addition, the abovementioned active substance formulations may comprise, if appropriate, the conventional adhesives, wetters, dispersants, emulsifiers, preservatives, antifreeze agents, solvents, fillers, colors, carriers, antifoams, evaporation inhibitors, pH regulators or viscosity regulators.

For example, it is known that the effect of glufosinate-ammonium (A1.2) and of its L-enantiomer can be improved by surfactants, preferably by wetters from the series of the alkyl polyglycol ether sulfates which contain, for example, 10 to 18 carbon atoms and which are used in the form of their alkali metal salts or ammonium salts, but also as the magnesium salt, such as sodium $C_{12}/C_{14}$-fatty alcohol diglycol ether sulfate (®Genapol LRO, Hoechst); see EP-A-0476555, EP-A-0048436, EP-A-0336151 or U.S. Pat. No. 4,400,196 and Proc. EWRS Symp. "Factors Affecting Herbicidal Activity and Selectivity", 227-232 (1988). Moreover, it is known that alkyl polyglycol ether sulfates are also suitable as penetrants and synergists for a series of other herbicides, inter alia also herbicides from the series of the imidazolinones; see EP-A-0502014.

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further prior to use with other inert substances.

The active substances can be applied to the plants, parts of the plants, seeds of the plants or the area under cultivation (soil of a field), preferably to the green plants and parts of the plants and, if appropriate, additionally to the soil of the field.

One possible use is the joint application of the active substances in the form of tank mixes, the concentrated formulations of the individual active substances, in optimal formulations, jointly being mixed with water in the tank and the resulting spray mixture being applied.

A joint herbicidal formulation of the combination according to the invention of the active substances (A) and (B) has the advantage of being easier to apply since the quantities of the components are already presented in the correct ratio to each other. Moreover, the adjuvants in the formulation can be matched optimally to each other, while a tank mix of different formulations may lead to undesired combinations of adjuvants.

A. GENERAL FORMULATION EXAMPLES a) A dust is obtained by mixing 10 parts by weight of an active substance/active substance mixture and 90 parts by weight of talc as inert material and comminuting the mixture in a hammer mill.

b) A wettable powder which is readily dispersible in water is obtained by mixing 25 parts by weight of an active substance/active substance mixture, 64 parts by weight of kaolin-containing quartz as inert material, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of an active substance/active substance mixture with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to 277 C), and grinding the mixture in a ball mill to a fineness of below 5 microns.

d) An emulsifiable concentrate is obtained from 15 parts by weight of an active substance/active substance mixture, 75 parts by weight of cyclohexanone as solvent and 10 parts by weight of oxethylated nonylphenol as emulsifier.

e) Water-dispersible granules are obtained by mixing
  75 parts by weight of an active substance/active substance mixture,
  10 parts by weight of calcium lignosulfonate,
  5 parts by weight of sodium lauryl sulfate,
  3 parts by weight of polyvinyl alcohol and
  7 parts by weight of kaolin,
  grinding the mixture on a pinned-disk mill and granulating the powder in a fluidized bed by spraying on water as granulation liquid.

f) Water-dispersible granules are also obtained by homogenizing and precomminuting, on a colloid mill,
  25 parts by weight of an active substance/active substance mixture,
  5 parts by weight of sodium 2,2'-dinaphthylmethane-6,6'-disulfonate,
  2 parts by weight of sodium oleoylmethyltaurinate,
  1 part by weight of polyvinyl alcohol,
  17 parts by weight of calcium carbonate and
  50 parts by weight of water, subsequently grinding the mixture in a bead mill and atomizing and drying the resulting suspension in a spray tower by means of a single-substance model.

Biological Examples

1. Pre-Emergence Effect on Weeds

Seeds or rhizome pieces of monocotyledonous and dicotyledonous weed plants are placed in sandy loam soil in plastic pots and covered with soil. The compositions which are formulated in the form of concentrated aqueous solutions, wettable powders or emulsion concentrates are then applied to the surface of the soil cover in the form of an aqueous solution, suspension or emulsion at an application rate of 600 to 800 l of water/ha (converted), in various dosages. After the treatment, the pots are placed in a greenhouse and kept under good growth conditions for the weeds. After the test plants have emerged, the damage to the plants or the negative effect on the emergence is scored visually after a test period of 3 to 4 weeks by comparison with untreated controls. As shown by the test results, the compositions according to the invention have a good herbicidal pre-emergence activity against a broad spectrum of grass weeds and dicotyledonous weeds.

Frequently, effects of the combinations according to the invention are observed which exceed the formal total of the effects when applying the herbicides individually (=synergistic effect).

If the data of the effects observed already exceed the formal total ($=E^A$) of the data of the experiments with individual applications, then they also exceed Colby's expected value ($=E^C$), which is calculated by the formula which follows and which is also considered to be suggestive of synergism (cf. S. R. Colby; in Weeds 15 (1967) pp. 20 to 22):

$$E = A + B - (A \cdot B / 100)$$

A, B denote the effect of the active substances A, or in %, for a or b g of a.s./ha; E denotes the expected value in % for a+b g a.s./ha.

At suitable low dosages, the observed data of the experiments show an effect of the combinations above Colby's expected values.

2. Post-Emergence Effect on Weeds

Seeds or rhizome pieces of monocotyledonous and dicotyledonous weeds are placed in sandy loam soil in cardboard pots, covered with soil and grown in the greenhouse under good growth conditions. Three weeks after sowing, the test plants in the three-leaf stage are treated with the compositions according to the invention. The compositions according to the invention which are formulated as wettable powders or as emulsion concentrates are sprayed in various dosages on the green parts of the plants at an application rate of 600 to 800 l of water/ha (converted). After the test plants have remained in the greenhouse for about 3 to 4 weeks under optimal growth conditions, the effect of the products is scored visually by comparison with untreated controls. When applied post-emergence, too, the compositions according to the invention have a good herbicidal activity against a broad spectrum of economically important grass weeds and broad-leaved weeds.

Frequently, effects of the combinations according to the invention are observed which exceed the formal total of the effects when applying the herbicides individually. At suitable low dosages, the observed data of the experiments show an effect of the combinations above Colby's expected values. (cf. score figures in Example 1).

3. Herbicidal Effect and Tolerance by Crop Plants
(Field Trial)

Transgenic cotton plants with a resistance to one or more herbicides (A) together with typical weed plants were grown in the open on 2×5 m plots under natural field conditions; alternatively, weed infestation occurred naturally when the cotton plants were grown. The treatment with the compositions according to the invention and, as control, separately by only applying the active substances of the components, was carried out under standard conditions with a plot sprayer at an application rate of 200-300 liters of water per hectare in parallel tests as can be seen from the scheme in Table 1, i.e. pre-sowing pre-emergence, post-sowing pre-emergence or post-emergence in the early, medium or late stage.

TABLE 1

Use scheme - examples

| Application of the active substances | Pre-sowing | Pre-emergence post-sowing | Post-emergence 1-2-leaf | Post-emergence 2-4-leaf | Post-emergence 6-leaf |
|---|---|---|---|---|---|
| combination | (A) + (B) | | | | |
| " | | (A) + (B) | | | |
| " | | | (A) + (B) | | |
| " | | | | (A) + (B) | |
| " | | | | | (A) + (B) |
| sequential | (A) | | (B) | | |
| " | | (A) | (B) | | |
| " | | (A) | | (B) | |
| " | | (A) | (A) | (B) | |
| " | | (A) | | (B) | (B) |
| " | | (A) | | (A) + (B) | |
| " | (B) | | (A) | | |
| " | | (B) | | (A) + (B) | |
| " | (A) + (B) | | (A) + (B) | | |
| " | (A) + (B) | (A) + (B) | (A) + (B) | | |
| " | | (A) + (B) | (A) + (B) | | |
| " | | (A) + (B) | (A) + (B) | (A) + (B) | |
| " | | (A) + (B) | (A) + (B) | (A) + (B) | (A) + (B) |
| " | | | (A) + (B) | (A) + (B) | |
| " | | | (A) + (B) | (A) + (B) | (A) + (B) |
| " | | | | (A) + (B) | (A) + (B) |

2, 4, 6 and 8 weeks after the application, the herbicidal activity of the active substances or active substance mixtures was scored visually with reference to the treated plots in comparison to untreated control plots. The damage to, and the development of, all aerial parts of the plants was recorded. Scoring was done on the basis of a percentage sale (100% action=all plants destroyed; 50% action=50% of the plants and green parts of the plants destroyed; 0% action=no recognizable effect=like control plot. The mean of the score values of in each case 4 plots was calculated.

The comparison demonstrated that the herbicidal effect of the combinations according to the invention was usually higher, in some cases considerably higher, than the total of the effects of the individual herbicides. In essential periods of the period of scoring, the effects were greater than Colby's expected values (cf. scoring in Example 1) and therefore suggest a synergism. In contrast, the cotton plants were not damaged owing to the treatments with the herbicidal compositions, or were only damaged to a negligible extent.

Abbreviations generally used in the following tables:

g of a.s./ha=gram of active substance (100% active substance) per hectare $E^A$=Total of the herbicidal effects of the individual applications $E^C$=Colby's expected value (cf. scoring in Table 1)

TABLE 2

Herbicidal effect in field trials with cotton

| Active substance(s) | Dose[1] g of a.s./ha | Herbicidal action[2] (%) against | |
|---|---|---|---|
| | | Echinocloa colonum | Datura stramonium |
| (A1.2) | 450 | 0 | 75 |
| | 600 | 15 | 90 |
| | 1000 | 30 | 100 |
| (B1.9) | 930 | 88 | 0 |
| (A1.2) + (B1.9) | 450 + 930 | 94 | 97 |

Abbreviations for Table 2:
[1]= Application in the 4-5-leaf stage
[2]= Scoring 3 weeks after application
(A1.2) = glufosinate-ammonium
(B1.9) = metolachlor

TABLE 3

Herbicidal effect in field trials with cotton

| Active substance(s) | Dose[1] g of a.s./ha | Herbicidal action[2] (%) against Sorghum halepense |
|---|---|---|
| (A1.2) | 500 | 53 |
| | 300 | 15 |
| (B4.2) | 125 | 58 |
| (A1.2) + (B4.2) | 300 + 125 | 100 (E = 73) |

Abbreviations for Table 3:
[1]= Application in the 4-leaf stage
[2]= Scoring 30 days after application
(A1.2)= glufosinate-ammonium
(B4.2)= cycloxydim
The treated cotton crop showed no significant damage.

TABLE 4

Herbicidal effect in field trials with cotton

| Active substance(s) | Dose[1] g of a.s./ha | Herbicidal action[2] (%) against Abutilon theophrasti |
|---|---|---|
| (A1.2) | 300 | 30 |
| (B2.1) | 120 | 45 |
| (A1.2) + (B2.1) | 300 + 120 | 83 (E = 75) |

Abbreviations for Table 4:
[1] = Application in the 4-5 leaf stage
[2] = Scoring 27 days after application
(A1.2) = glufosinate-ammonium
(B2.1) = lactofen
The treated cotton crop showed no significant damage.

TABLE 5

Herbicidal effect in field trials with cotton

| Active substance(s) | Dose[1] g of a.s./ha | Herbicidal action[2] (%) against Ipomoea hederacea |
|---|---|---|
| (A1.2) | 600 | 75 |
| | 400 | 43 |
| (B1.12) | 925 | 42 |
| (A1.2) + (B1.12) | 400 + 925 | 100 ($E^A$ = 85) |
| (B2.4) | 105 | 42 |
| (A1.2) + (B2.4) | 400 + 105 | 95 ($E^A$ = 85) |
| (B1.2) | 1120 | 37 |
| (A1.2) + (B1.2) | 400 + 1120 | 88 ($E^A$ = 80) |
| (A3.5) | 35 | 42 |
| (A1.2) + (A3.5) | 400 + 35 | 93 ($E^A$ = 85) |
| (B5.1) | 560 | 32 |
| (A1.2) + (B5.1) | 400 + 560 | 78 ($E^A$ = 75) |

Abbreviations for Table 5:
[1]= Application in the 4-leaf stage
[2]= Scoring 23 days after application
(A1.2) = glufosinate-ammonium
(B1.12) = pendimethalin
(B2.4) = pyrithiobac
(B1.2) = fluometuron
(A3.5) = imazamox
(B5.1) = bromoxynil

The invention claimed is:

1. A herbicidal composition which comprises
(A) one or more broad-spectrum herbicides selected from the group of the compounds consisting of:
(A1) compounds of the formula (A1):

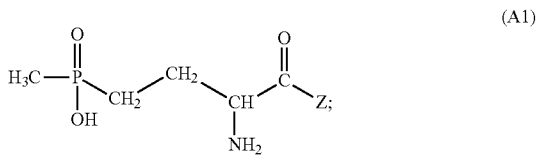

in which Z is a radical of the formula —OH, or the salts thereof; and
(B) one or more herbicides selected from the group of the compounds which consists of:
(B4) cycloxydim and clethodim; wherein the combination of herbicides (A) and (B) provides a synergistic effect and gives a greater activity than the herbicide (A) and the herbicide (B) alone.

2. The herbicidal composition as claimed in claim 1; wherein glufosinate-ammonium is employed as active substance (A).

3. The herbicidal composition as claimed in claim 1; wherein the cycloxydim is employed as component (B).

4. The herbicidal composition as claimed in claim 2; wherein the cycloxydim is employed as component (B).

5. The herbicidal composition as claimed in claim 1; wherein the clethodim is employed as component (B).

6. The herbicidal composition as claimed in claim 2; wherein the clethodim is employed as component (B).

* * * * *